United States Patent [19]
Wassenberg, II

[11] Patent Number: 4,747,918
[45] Date of Patent: May 31, 1988

[54] ELECTROELUTION APPARATUS AND METHOD OF USING SAME

[75] Inventor: Donald R. Wassenberg, II, San Diego, Calif.

[73] Assignee: William Bellomy, San Diego, Calif.

[21] Appl. No.: 875,617

[22] Filed: Jun. 18, 1986

[51] Int. Cl.⁴ .................. G01N 27/28; G01N 27/30
[52] U.S. Cl. ........................ 204/182.8; 204/299 R; 436/516; 436/515
[58] Field of Search .............. 204/299 R, 182.8; 436/516, 515

[56] References Cited

U.S. PATENT DOCUMENTS

| | | | |
|---|---|---|---|
| 3,657,260 | 4/1972 | McLeester. | |
| 3,969,218 | 7/1976 | Scott | 204/299 R |
| 3,989,612 | 11/1976 | Kragt | 204/299 R |
| 4,049,534 | 9/1977 | Posner | 204/299 R |
| 4,130,471 | 12/1978 | Grunbaum | 204/180 G |
| 4,234,400 | 11/1980 | Kaplan et al. | 204/180 G |
| 4,294,684 | 10/1981 | Serwer | 204/299 R |
| 4,391,688 | 7/1983 | Hamelin | 204/180 G |
| 4,495,279 | 1/1985 | Karpetsky et al. | 435/6 |
| 4,545,888 | 10/1985 | Walsh | 204/301 |
| 4,576,702 | 3/1986 | Peck et al. | 204/299 R |

Primary Examiner—John F. Niebling
Assistant Examiner—Ben C. Hsing
Attorney, Agent, or Firm—Knobbe, Martens, Olson & Bear

[57] ABSTRACT

An electroelution apparatus having at least one container for receiving a liquid, wherein the liquid volume of the container is less than 50 ml, a first electrode in the container on one side of the container and a second electrode in the container on the other side of the container, means for applying a sufficient voltage to the first and second electrodes to electrophoretically elute a charged biological molecule from a gel placed between the first and second electrodes, and means for interrupting the application of the voltage to the first and second electrodes. The elution time is 10 minutes or less, and the ratio of the volume of the gel to the volume of the liquid is greater than 1:100. Also disclosed is a method for eluting a charged biological molecule from a gel, comprising the steps of placing the gel in the container of the disclosed apparatus, substantially immersing at least a portion of the gel containing the biological molecule in a liquid, wherein the total volume of liquid is less than 50 ml, applying a voltage to the electrodes for a time of 10 minutes or less, and eluting the biological molecule.

13 Claims, 1 Drawing Sheet

U.S. Patent
May 31, 1988
4,747,918
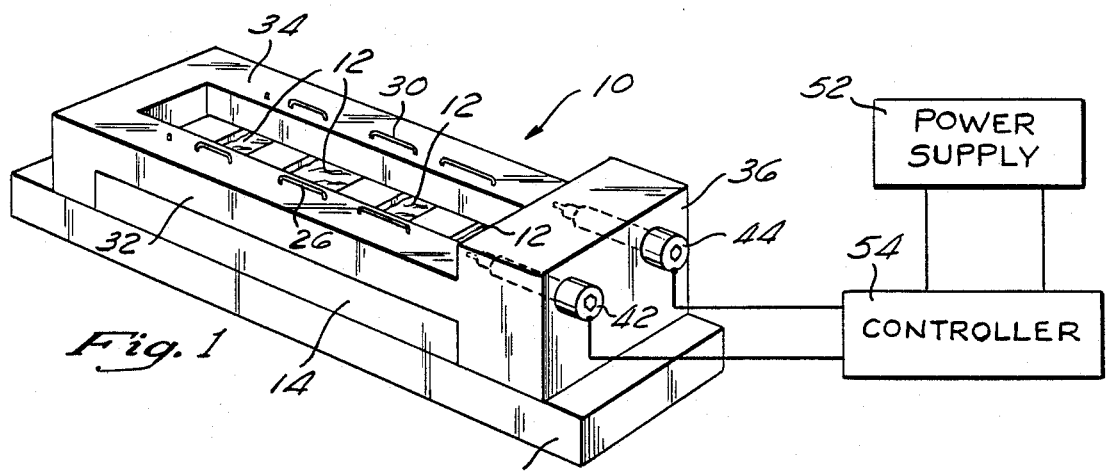
Fig. 1
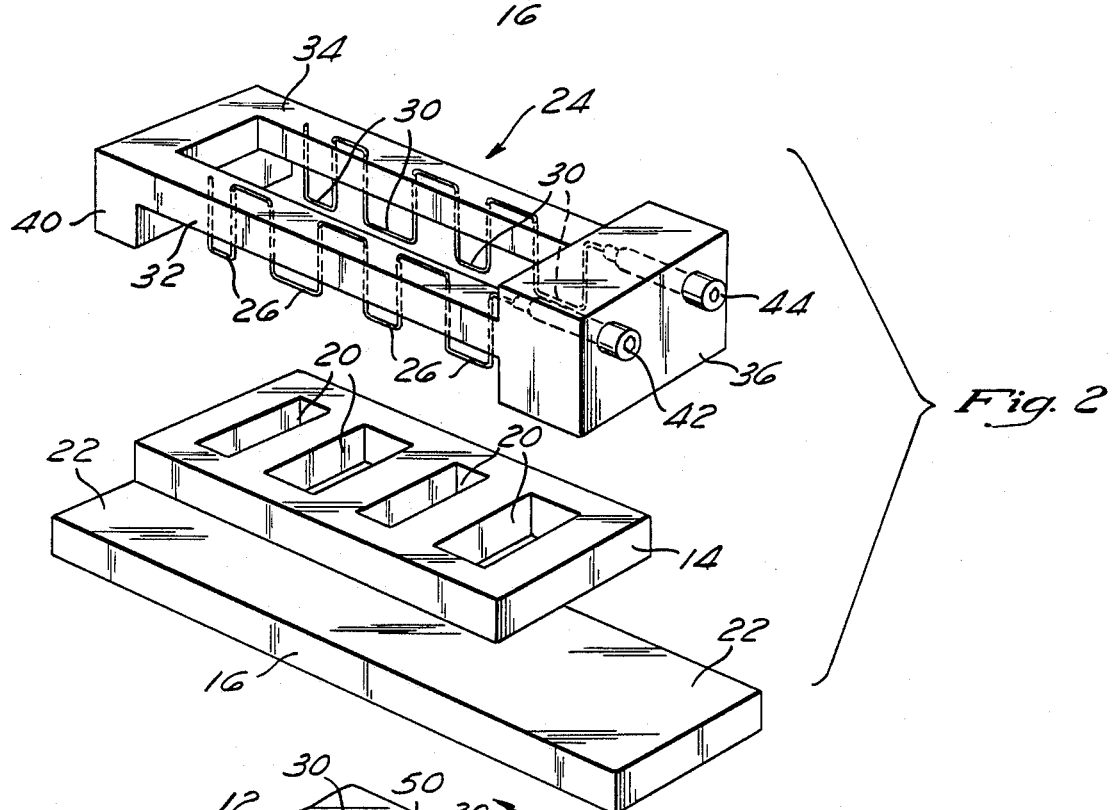
Fig. 2
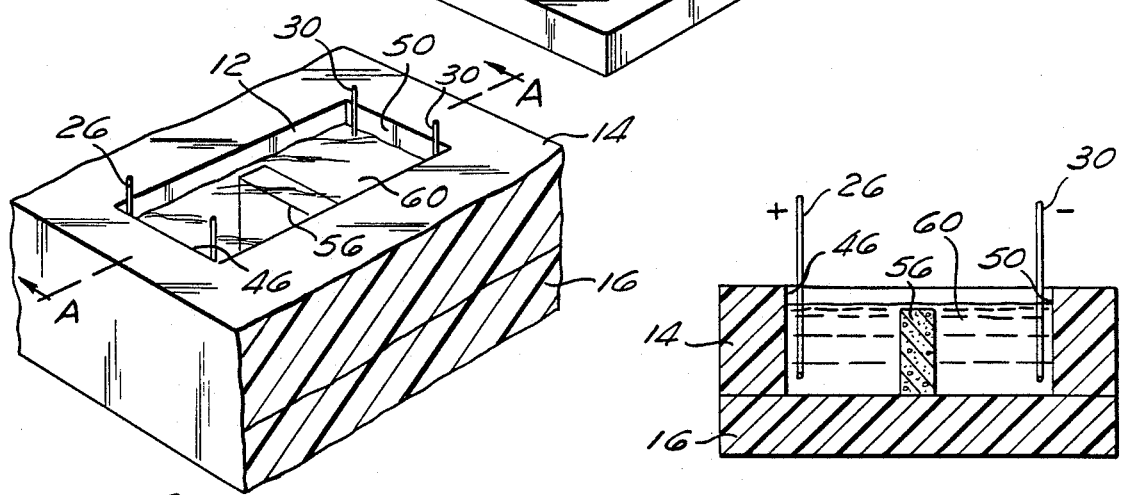
Fig. 3
Fig. 4

ELECTROELUTION APPARATUS AND METHOD OF USING SAME

BACKGROUND OF THE INVENTION

This invention relates to the field of gel electrophoresis, and specifically to an apparatus and method for the elution and recovery of molecules isolated in such gels.

Gel electrophoresis is a technique for separating charged molecules having different charges or different molecular weights. It is commonly used for biological molecules, including proteins and nucleic acid polymers (such as DNA and RNA).

In gel electrophoresis, the commonly used gels are agarose gels and polyacrylamide gels. The gel may be thought of as a complex network of polymer molecules in which the channels between the molecules are occupied by a liquid such as a buffered aqueous solution. Electrodes are placed in a buffered aqueous solution, and the gel (which is also in the solution) is interposed between the electrodes. In effect, the gel is interposed in the current flow path between the electrodes and it separates the aqueous buffer solution in which the anode is placed from the aqueous buffer solution in which the cathode is placed.

A well or indentation is ordinarily provided in the gel, into which the sample is introduced. When a potential is applied to the electrodes, an electrical field is created through the gel and, under the influence of that field, charged molecules in the sample move through the gel. For example, negatively charged DNA molecules move through the gel toward the cathode. The rate of movement through the gel depends upon the molecular weight of the molecule. Migrating macromolecules must pass through a labyrinth of passageways in the gel. Because small molecules can traverse such a maze more rapidly than larger molecules, the rate of migration through the gel depends on the molecular weight of the molecule. For unknown reasons, the distance "D" moved by a molecule having molecular weight "M" depends logarithmically on M, according to the equation:

$$D = a - b \log M,$$

in which a and b are empirically determined constants which depend on the temperature, the buffer used, and the makeup of the gel. As a result of such differential migration of molecules through the gel, sample molecules of different molecular weights become distributed throughout the gel in "bands". The electrophoresis process is ordinarily discontinued while the molecules of interest are located in a band or bands in the gel and before those molecules leave the gel and enter the buffer solution on the other side of the gel.

At that point in the process, the bands may be visualized by any appropriate visualization technique, such as by staining or by radioactive labeling and visualization. The gel is then physically cut into sections which contain only one band, and the sections containing molecules of interest are retained.

In order to recover the molecules at this point, it is necessary to elute them from the gel.

Prior art electroelution devices typically employ two large baths of buffer, each bath containing an electrode. The gel slice from which the molecule of interest is to be eluted ordinarily has been interposed between the electrodes in such a way that is creates a fluid seal between the baths. When a potential is applied to the electrodes, the molecule moves through the gel toward the electrode having a charge opposite to the charge of the molecule. This movement takes it out of the gel and into the buffer solution. The volume of the two buffer baths, in comparison to the volume of the gel, is high. The ratio of bath volume to gel volume is usually over 1000:1. Because of the large volume of buffer in the bath into which the molecule is eluted, various methods have been devised in the prior art to trap or catch the molecule of interest. For example, in U.S. Pat. No. 3,969,218, molecules leaving the gel are shunted by flowing liquid away from the electrode and into a separate receptacle. U.S. Pat. No. 4,049,534 discloses trapping the eluted molecules with a dialysis membrane interposed between the gel and the electrode. In U.S. Pat. No. 4,545,888, filter discs of DEAE cellulose are provided between the gel and the electrode to trap eluted DNA molecules. One commercial device, the International Biotechnologies, Inc. electroelutor, seeks to trap the eluted molecules in a saline solution interposed between the gel and the electrode.

The elution time in these devices is often between twenty minutes and one hour. During elution, substantial electrolysis with attendant bubble generation occurs. Moreover, the buffer solutions and the gels are heated by the current flow between the electrodes. This has the potential for damaging the biological molecules being eluted. For this reason, the baths in which the electrodes are placed are ordinarily very large, in order to provide a heat sink capability.

Great pains have been taken in the prior art to prevent contact between the eluted molecules and the electrodes. It is apparently the common understanding in the art that such molecule-electrode contact can lead to degradation or other damage to the molecule.

SUMMARY OF THE INVENTION

I have discovered that many of the preconceived notions in the art regarding electrophoresis and electroelution are inaccurate or untrue. Specifically, I have discovered a method and apparatus for the electroelution of biological molecules from a gel wherein the volume of the bath into which the molecule is eluted is at least one order, and preferably several orders, of magnitude smaller than the baths used in the prior art. I have also successfully reduced the elution time to only a fraction of the time required in prior art machines, while avoiding overheating of the bath. The apparatus I use is simpler, more foolproof, and quicker than the prior art devices, permitting a much higher percentage of recovery of eluted molecules while eliminating cross-contamination problems.

In accordance with one aspect of the present invention, there is provided an electroelution apparatus, comprising at least one container (and preferably several containers) for receiving a liquid, each container having a first side and a second side, where the liquid volume of each container is less than about 50 ml, preferably a maximum of about 20 ml or 10 ml, more preferably a maximum of about 5 ml or 3 ml, and most preferably a maximum of about 2 ml or 1 ml. A first electrode is provided in each container on the first side of the container and a second electrode is provided in each container on the second side of that container. Also provided is a means for applying a sufficient voltage between the first and second electrodes to electrophoretically elute a biological molecule from a gel placed between the first and second electrodes, and a means for interrupting the application of the voltage to the electrodes. The means for interrupting the voltage applied to the electrodes can be a simple switch, a switch actuated by a timer, or a switch actuated by a detector that senses when the molecule of interest has been eluted.

In a preferred embodiment of the invention, the electroelution apparatus comprises at least 2, and preferably at least 3, containers in a single system or unit. The electrodes for each container may be connected to a common power supply.

The voltage applied to the electrodes is preferably between about 5 volts and about 100 volts, more preferably between about 10 volts and about 50 volts, and most preferably between about 10 volts and about 30 volts.

In a particularly preferred embodiment, the electroelution apparatus comprises a base portion having a substantially flat top surface, a receptacle portion comprising a flat sheet having a plurality of holes therethrough, the receptacle portion having a thickness of no more than 5 cm, the receptacle portion being connected to the top surface of the base portion so that the holes in the receptacle portion comprise containers wherein the bottom of each container is the top surface of the base portion, and an electrode assembly adapted to fit into the receptacle portion. The electrode assembly comprises a plurality of first electrodes electrically connected to a common point, and a plurality of second electrodes electrically connected to a second common point, so arranged that when the electrode assembly is placed on the receptacle, a first electrode and a second electrode extend into each of the holes in the receptacle. The volume of each of the containers is preferably less than about 5 ml.

In accordance with another aspect of the present invention, there is provided a method for the electrophoretic elution of a charged biological molecule from a gel, comprising the steps of providing a container for liquid, the container having a first side and a second side, with a first electrode on the first side of the container and a second electrode on the second side of the container, placing the gel containing the charged biological molecule in the container and substantially immersing at least the portion of the gel containing the biological molecule in a liquid in the container, wherein the total volume of the liquid in the container is less than about 50 ml, preferably less than about 10 ml or 5 ml, and most preferably less than about 3 ml or 2 ml. In a particularly preferred embodiment, the volume of liquid in the container is less than about 1 ml. The method also includes the steps of applying the voltage to the electrodes for a period of time sufficient to elute the biological molecule from the gel into the liquid, and removing the liquid containing the molecule from the container. The voltage is preferably applied to the electrodes for a maximum of about 10 minutes or about 5 minutes, more preferably for a maximum of about 3 minutes and most preferably for a maximum of about 2 minutes. Optionally included within the method are the steps of permitting some of the biological molecules to contact one of the electrodes, and the step of monitoring the location of the biological molecule and discontinuing the application of a voltage to the electrodes when the biological molecule has entered the liquid.

In the method of the present invention, the ratio of the volume of the gel to the volume of the liquid in which the gel is placed is greater than about 1:100, preferably greater than about 1:50, and most preferably greater than about 1:30. The voltage applied to the electrodes is preferably between about 5 volts and about 100 volts, more preferably between about 10 volts and about 50 volts, and most preferably between about 10 volts and about 30 volts.

BRIEF DESCRIPTION OF THE DRAWINGS

FIG. 1 is a perspective view of the electroelution apparatus of the present invention.

FIG. 2 is an exploded view of the electroelution apparatus of FIG. 1.

FIG. 3 is a perspective view of a portion of the apparatus shown in FIG. 1, illustrating an individual container of the electroelution apparatus.

FIG. 4 is a sectional view of the electroelution container shown in FIG. 3 taken along the line A—A.

DETAILED DESCRIPTION OF THE PREFERRED EMBODIMENTS

With reference to FIG. 1, the electroelution apparatus 10 of the present invention comprises one or more containers 12 formed in a receptacle 14 supported by a base 16. The containers 12 are discrete in that there is no liquid connection between the chambers. As shown in FIG. 2, the receptacle 14 may be a flat sheet having one or more holes 20 therethrough. The receptacle 14 preferably has a thickness of no more than about 5 cm, preferably no more than about 3 cm, and most preferably about 2 cm. When the receptacle 14 is connected to the base 16, the sides of the holes 20 in combination with the top of the base 16 form the containers 12, so that the bottom of each container 12 is the top surface of the base 16.

In a preferred embodiment, at least one side 22, and preferably at least two sides 22, of the base 16 extend beyond the receptacle 14. Although the figures illustrate that the base 14 and the receptacle 16 are formed from separate pieces of material, it will be understood that the base 14 and receptacle 16 can readily be formed from a single piece of material by conventional techniques. Suitable materials for the electroelution apparatus 10 include the plastics and other synthetic polymers, including nylon, polycarbonate, polyethylene, polypropylene, polyvinylchloride, and the acrylics; as well as various metals, such as stainless steel, and ceramics.

An electrode assembly 24 is also provided. This electrode assembly is adapted to fit over the receptacle 14. The electrode assembly 24 includes a plurality of first electrodes 26 and a plurality of second electrodes 30. The electrode assembly 24 includes a first strut 32 carrying said first electrodes and a second strut 32 carrying said second electrodes. The first strut 32 and the second strut 34 run parallel to each other and are spaced apart from each other. The electrodes 26, 30 extend downwardly from the struts 32, 34. Connecting the ends of the struts 32, 34 are a first end piece 36 and a second end piece 40. The distance between the end pieces 36, 40 (and thus the length of the struts 32, 34) is the same as the length of the receptacle 14.

The entire electrode assembly 24 is constructed to fit over the receptacle 14, and may be removable. The electrodes 26, 30 and the end pieces 36, 40 extend below the bottom of the struts 32, 34, so that when the electrode assembly 24 is placed on the receptacle 14, the electrodes 26, 30 extend into the containers 12, the struts 32, 34 rest on the top of the receptacle 14, and the end pieces 36, 40 rest on the sides 22 of the base 16 extending beyond the receptacle 14.

In a preferred embodiment, all of the first electrodes 26 may be electrically connected to a first common point 42, and all of the second electrodes 30 may be electrically connected to a second common point 44. (See FIG. 2.) The common points 42, 44 may be conventional electrical connectors, such as posts, plugs or jacks.

All of the first electrodes 26 may advantageously be formed from a single piece of metal, such as a platinum wire, and all of the second electrodes 30 may similarly be formed from a single piece of metal, such as a platinum wire. The platinum wire (or other suitable electrode material, such as gold) may be bent to form the two sets of electrodes so that a loop of wire forming each electrode 26, 30 extends down from the struts 32, 34 in alignment with each container 12. Alternatively, the two sets of electrodes 26, 30 may be of discrete material, but with all electrodes in each set being connected either in series or in parallel to the appropriate common point 42, 44.

With reference to FIGS. 3 and 4, each of the containers 12 (which are preferably rectangular) have a first end 46 and a second end 50. In each container 12, a first electrode 26 is located at the first end 46 of the container 12, and a second electrode 30 is located at the second end 50 of the container 12.

The dimensions of each of the containers are selected according to the size of the gel slice that will be placed in the container for electroelution. However, it is preferred that the containers do not exceed about 5 cm, and preferably that they do not exceed about 3 cm, in any dimension. The volume of the containers 12 is less than about 50 ml, preferably less than about 10 ml or about 5 ml, and most preferably less than about 3 ml or about 2 ml. In a particularly preferred embodiment, the volume of the containers 12 is less than about 1 ml, and highly successful electroelution has been accomplished with a liquid volume in the container of less than about 0.4 ml.

With reference to FIG. 1, a power supply 52 is provided for supplying power to the electrodes 26, 30. The power supply is capable of delivering a predetermined voltage to the electrodes 26, 30 and is preferably electrically connected to the first common point 42 and the second common point 44. The voltage delivered by the power supply is preferably between about 5 volts and about 100 volts, DC, and the power supply may be adjustable to provide any desirable voltage in that range. It is preferred that the voltage be between about 10 volts and about 50 volts, and it is most preferred that the voltage be between about 10 volts and about 30 volts.

A controller 54 may also be provided for controlling the application of a voltage to the electrodes. The controller may be a simple switch, capable of interrupting the application of a voltage to the electrodes 26, 30 or it may be a timer, interrupting the voltage after a predetermined time. Where the molecule being eluted has been labeled, either radioactively or optically, the controller 54 may include a radioactive or optical sensor (not shown) in the proximity of the electrode having a charge opposite to the molecule being eluted. In this way, the voltage can be automatically interrupted when elution is complete.

The first step in eluting the charged biological molecule from an electrophoresis gel is to obtain a slice of gel containing only the molecule of interest. Usually, the gel slice is about 6 to 7 mm tall, about 7 to 10 mm wide, and about 4 mm thick. With reference to FIGS. 3 and 4, the gel 56 containing the charged biological molecule to be eluted is placed in the container 12. The gel 56 is preferably oriented so that the side of the gel most adjacent to the biological molecule is oriented toward the electrode having a charge opposite to that of the biological molecule. In that way, the elution time is minimized because the thickness of gel the molecule is required to traverse is relatively small. The gel 56 need not be attached to or immobilized by the container 12.

A buffer solution 60 is provided in the container 12 with the gel 56. The gel 56 is situated between the electrodes, and the buffer 60 surrounds the gel. Suitable buffers are well known in the art. A preferred buffer for elution of DNA is 20 mM NaCl, 5 mM tris-Cl, and 1 mM EDTA.

The gel 56 is preferably situated in the container 12 in such a way that it does not completely block the movement of buffer from one side of the gel 56 to the other side. In other words, a small space between the edge of the gel 56 and the edge of the container 12 is preferred. Containers 12 of various sizes may be provided in the same electroelution apparatus 10 in order to accommodate gels 56 of different sizes.

With the gel 56 in the buffer 60, the electroelution process may proceed. Elution is accomplished by applying a voltage to the electrodes 26, 30 to create a potential difference between the electrodes 26, 30. The charged biological molecule in the gel 56 moves under the influence of the resulting electric field toward the electrode having a charge opposite to that of the molecule. Thus, DNA (which is negatively charged) will move toward the cathode, which is the first electrode 26 in FIG. 4. Because heat is generated by current flow through the buffer 60 and the gel 56, the buffer is preferably chilled prior to initiation of elution. The gel also may be chilled if desired. The appropriate voltage for elution may be empirically determined in each particular case. However, as a general rule, voltages between 5 volts and 100 volts are appropriate. Voltages between 10 and 50 volts, and particularly between 10 and 30 volts, work very well. For example, with a 0.4 ml buffer volume, and a potential of 25 volts between the electrodes, elution is accomplished in less than one minute.

The preferred elution time is the minimum time necessary for the molecule of interest to migrate from the gel 56 into the buffer 60. The elution time, of course, is directly related to the applied voltage. Moreover, because the temperature of a small volume of buffer will increase during elution more rapidly than a large volume of buffer, the maximum permissible elution time is related to the buffer volume. However, in the apparatus of the present invention, the voltage is applied to the electrodes for no more than about 10 minutes, preferably for a maximum of about 5 minutes or about 3 minutes, and most preferably for a maximum of about 2 minutes or about 1 minute. Where the molecule to be eluted has been labeled with a dye (such as an ultraviolet dye) or a radioactive label, the movement of the molecule through the gel and into the liquid can be observed. In that situation, the power supply 52 can be disconnected or turned off manually once the molecule of interest has left the gel 56 and entered the buffer 60. Alternatively, a photoreceptor or radiation detector comprising a part of controller 54 may be utilized to automatically determine when elution is complete.

Contrary to the conventional wisdom in the art, I have discovered that it is not necessary to prevent all contact between the biological molecule and the electrode, so discontinuance of elution prior to such contact is not necessary. Nevertheless, it is desirable to discontinue elution to avoid prolonged molecule-electrode contact.

In the method of the present invention, the ratio of gel volume to buffer volume is very large. The volume of the gel 56 to the volume of the buffer or other liquid 60 is greater than 1:100, preferably greater than 1:50, and most preferably greater than 1:30.

When used to elute DNA, the buffer solution removed from the container after elution is completed usually contains from 10 to 30 μg/ml DNA. Ordinarily, DNA can be precipitated directly from a solution having a concentration of at least 1.5 μg/ml DNA. Thus, unlike prior art electroelution devices, the present electroelution device permits direct precipitation of DNA from the buffer into which the DNA was eluted. This eliminates time-consuming and wasteful post-elution concentration steps.

For DNA, the precipitation steps involve diluting the buffer with 2.5 times its volume of ethanol, and 0.4 times its volume of 5 M NaCl. Thus, when the volume of the eluant is 0.4 ml (as is common with the present invention), precipitation of all the DNA in a single 1.5 ml Epindorf tube is feasible. Recovery of 80–95% of the DNA in the gel is feasible with the present invention. This compares favorably to prior art electroelution devices, which often have recovery efficiencies in the neighborhood of 40–50%.

Although the present invention has been described in the context of certain preferred embodiments, it will be apparent to those of ordinary skill in the art that various modifications and changes are possible without departure from the spirit of the invention. Accordingly, it is intended that the scope of the present patent be determined by reference to the claims which follow.

What is claimed is:

1. A method for electrophoretic elution of a charged biological molecule from a gel, comprising the steps of:
    (a) providing a container for a liquid, said container having a first side and a second side, with a first electrode on said first side of said container and a second electrode on said second side of said container;
    (b) freely placing said gel in said container between said electrodes so that said gel is sitting unrestrained in said container and substantially immersing at least the portion of said gel containing said biological molecule in a single liquid in said container while permitting free movement of liquid around said gel during elution, wherein the total volume of liquid in said container and in fluid communication with said gel is less than 10 ml;
    (c) applying a voltage to said electrodes for a period of time sufficient to elute said biological molecule from said gel into said liquid; and
    (d) removing said liquid containing said molecule from said container.

2. The method of claim 1, wherein the volume of said liquid in said container is less than 5 ml.

3. The method of claim 1, wherein the volume of liquid in said container is less than 3 ml.

4. The method of claim 1, wherein the volume of liquid in said container is less than 2 ml.

5. The method of claim 1, wherein the volume of liquid in said container is less than 1 ml.

6. The method of claim 1, wherein the ratio of the volume of said gel to the volume of said liquid is greater than 1:100.

7. The method of claim 6, wherein the ratio of the volume of said gel to the volume of said liquid is greater than 1:50.

8. The method of claim 1, wherein said voltage is applied for a maximum of three minutes.

9. The method of claim 1, wherein said voltage is applied for a maximum of two minutes.

10. The method of claim 1, further comprising the step of permitting some of said biological molecules to contact one of said electrodes.

11. The method of claim 1, further comprising the step of monitoring the location of said biological molecule and discontinuing the application of a voltage to said electrodes when said biological molecule has entered said liquid.

12. An electroelution apparatus, comprising:
    a base portion having a substantially flat top surface;
    a receptacle portion comprising a flat sheet having a plurality of holes therethrough, said receptacle portion having a thickness of no more than 5 cm, said receptacle portion being connected to the top surface of said base portion so that said holes in said receptacle portion comprise containers wherein the bottom of each said container is the top surface of said base portion; and
    a separate electrode assembly adapted to fit onto said receptacle portion, said electrode assembly comprising a plurality of first electrodes electrically connected to a first common point, and a plurality of second electrodes electrically connected to a second common point, so that when said electrode assembly is placed on said receptacle, a first electrode and a second electrode extends into each of said holes in said receptacle.

13. The apparatus of claim 12, wherein the volume of each of said containers is less than 5 ml.

* * * * *